United States Patent [19]
Huang et al.

[11] Patent Number: 6,074,610
[45] Date of Patent: Jun. 13, 2000

[54] MULTI-SAMPLE REACTOR

[75] Inventors: Wuu-Liang Huang, Houston; Glenn A. Otten, The Woodlands, both of Tex.

[73] Assignee: ExxonMobil Upstream Research Company, Houston, Tex.

[21] Appl. No.: 09/073,634

[22] Filed: May 6, 1998

Related U.S. Application Data

[60] Provisional application No. 60/047,636, May 22, 1997.

[51] Int. Cl.$^7$ ...................................................... B01L 7/00
[52] U.S. Cl. ................................ 422/99; 422/63; 422/78; 422/104
[58] Field of Search ............................... 422/99, 109, 173, 422/198, 207, 266, 297, 307, 63, 78, 104; 436/30, 31

[56] References Cited

U.S. PATENT DOCUMENTS

| | | | |
|---|---|---|---|
| 4,710,354 | 12/1987 | Behar et al. ................................ | 422/80 |
| 4,835,707 | 5/1989 | Amano et al. ........................... | 364/497 |
| 5,395,586 | 3/1995 | Hemzy et al. ............................. | 422/63 |
| 5,779,982 | 7/1998 | Aota et al. ............................... | 422/100 |

OTHER PUBLICATIONS

Holloway, J.R., Dixon, J.E. and Pawley, A.R. (1992) An internal heated, rapid-quench, high-pressure vessel. *Am. Mineralogist*, V. 77, pp. 643–646. Month unavailable.

Horsfield, B., Disko, U. and Leistner, F. (1989) The microscale simulation of maturation: Outline of a new technique and its potential applications. *Geol. Rundsch.* v. 78, pp. 361–374. Month unavailable.

*Primary Examiner*—Robert J. Warden, Sr.
*Assistant Examiner*—Kaj K. Olsen
*Attorney, Agent, or Firm*—Charles R. Schweppe

[57] ABSTRACT

A reactor for subjecting multiple reactant samples to controlled conditions with respect to pressure, temperature, and time. All individual samples in a single test run are exposed to the same temperature and pressure profiles but can be independently and selectively quenched at different times during the test run.

15 Claims, 3 Drawing Sheets

MULTI-SAMPLE REACTOR

This application claims the benefit of U.S. Provisional Application No. 60/047,636, filed May 22, 1997.

FIELD OF INVENTION

This invention relates generally to the field of analytical chemistry. More particularly, the invention pertains to a multi-sample reactor capable of simultaneously subjecting multiple reactant samples to controlled pressure and/or temperature conditions.

BACKGROUND OF THE INVENTION

Several reactor systems have been used to subject reactant samples to elevated temperatures and pressures in order to perform a variety of experimental processes for both academic and industrial research. These processes include, but are not limited to, synthesis of new materials, determinations of stability and phase compatibility of various materials, pressure-volume-temperature studies, determinations of material solubilities, high pressure differential thermal analyses, electrical conductivity measurements, accelerated corrosion testing, special environmental testing, crystal growth in neutral or pressure media, and numerous geological tests and simulations associated with predicting oil field characteristics.

Geoscientists use such reactors for performing experiments and research in mineralogy, geochemistry, oil and gas generation, and cracking reaction kinetics. Such reactors are used to expose geological samples to pressure and temperature conditions to test theoretical predictions and simulate the results of natural geological processes, such as oil and gas generation kinetics and yields, clay transformation kinetics, fluid-rock interactions, organic pyrolysis, and the like. Such test results are an integral step in identifying and developing economic oil and gas resources.

Conventional equipment used to perform these various experiments includes cold seal reactors, hydrothermal pressure vessels, internally heated rapid-quench vessels, and the like. Cold seal reactors are typically less than 18 inches (46 cm) in length with an outside diameter of less than 3 inches (7.6 cm). Models MRA and LRA high pressure reactor vessels, available from LECO Corporation, Bellefonte, Pa., are examples of typical cold seal reactors. The heating rates for samples enclosed in cold seal type vessels are limited by the thermal mass of the vessel since the entire vessel must be heated. Cold seal reactors are usually adapted for use with single samples and typically require rapid cooling of the entire reactor vessel in order to quench the sample.

Hydrothermal pressure vessels include Dickson-type vessels and Parr™ pressure vessels. For additional detail on Dickson-type vessels, see Seyfried, Gordon, and Dickson, "A New Reaction Cell for Hydrothermal Solution Equipment," *American Mineralogist*, Vol. 64, pages 646–649 (1979). For additional details on Parr™ pressure vessels, see *Parr Instrument Company* 1991 *Catalog*, 7th ed., page 105. Hydrothermal pressure vessels are subject to the same heating rate and quenching limitations as discussed above for cold seal reactors.

An internally heated rapid-quench vessel is disclosed in Holloway, Dixon, and Pawley, "An Internally Heated, Rapid-Quench, High-Pressure Vessel," *American Mineralogist*, Vol. 77, pages 643–646 (1992). Internally heated rapid-quench vessels, such as disclosed in Holloway, et al., provide improved control of the heating rate of the sample since only the interior space in the vessel is heated thus eliminating the need to heat the entire mass of the vessel itself. However, control of the heating rate could be improved further if there were more direct or more intimate contact between the heat source and the sample. Additionally, the system shown in Holloway et al. is only adapted for use with individual reactant samples.

Persons skilled in analytical chemistry will readily understand that confirming predictions and developing confidence in various theories usually requires that the relevant experimental processes be performed repetitively. Repetitions of these tests may be performed at the same, or different, pressures and temperatures and in both cases, for varying periods of time. A common limitation of existing systems in performing such experiments on a repetitive basis is that these systems are designed to run only one sample at one set of pressure-temperature-time conditions. This limitation results in significant manpower requirements in order to prepare each sample and each experiment individually. Furthermore, limitations on available time for obtaining desired results may dictate the need for multiple pieces of test equipment in order to run numerous tests in parallel instead of in series.

Accordingly, in order to reduce the total time required for multiple tests and to reduce both the manpower and equipment costs associated with multiple tests, a need exists for equipment capable of simultaneously performing experiments upon multiple samples while varying testing conditions of pressure, temperature, and/or time. The present invention satisfies this need.

SUMMARY OF THE INVENTION

The present invention is a reactor capable of simultaneously subjecting multiple reactant samples to controlled pressure and temperature conditions. Typically, the reactor includes a pressure vessel having both a hot zone and a quench zone inside the vessel where test pressures ranging from above to below atmospheric pressure are desired. Heat is supplied to the hot zone and removed from the quench zone by any common method known to those skilled in the art and typically used in laboratory-scale reactors. A sample holder capable of holding two or more samples is mounted within the hot zone. The invention is also equipped with a sample release mechanism for selectively moving individual samples from the holder to the quench zone at a time or times determined by the operator. However, the reactor need not include a pressure vessel in all cases. Where operation at atmospheric pressure is desired, the sample holder can be attached to a support with the source of heat applied directly to the sample holder, and the selective removal of the samples from the holder allows the samples to cool at room temperature or be placed in another cooling medium.

In one preferred embodiment, the hot zone is located above the quench zone. Multiple reactant samples can be held in individual chambers in the holder by a sample retaining support. The chambers are arranged in a circular pattern around a generally vertical axis. The holder and the support are mounted to allow rotation with respect to one another about this axis. The support is provided with at least one opening that sequentially aligns with each of the chambers during this rotation, allowing individual samples to drop from the holder to the quench zone.

BRIEF DESCRIPTION OF THE DRAWINGS

The present invention and its advantages will be better understood by referring to the following detailed description and the attached drawings as described below.

FIGS. 1, 2, 3A, and 3B are not drawn to scale and are included only to illustrate the general arrangement of components for the various embodiments of the invention. One skilled in the art would recognize that variations of dimensions and substitutions of particular components with other configurations that perform essentially the same function would be included within the scope of the invention. To the extent that the following detailed description is specific to a particular embodiment or a particular use of the invention, this is intended to be illustrative only, and is not to be construed as limiting the scope of the invention. On the contrary, it is intended to cover all alternatives, modifications, and equivalents which may be included within the spirit and scope of the invention, as defined by the appended claims.

DETAILED DESCRIPTION OF THE PREFERRED EMBODIMENTS

The multi-sample pressure reactor of this invention, as illustrated in FIGS. 1, 2, 3A, and 3B and described in the text below, is adapted for use in processes or experiments to be performed on multiple test specimens.

Figure 1:
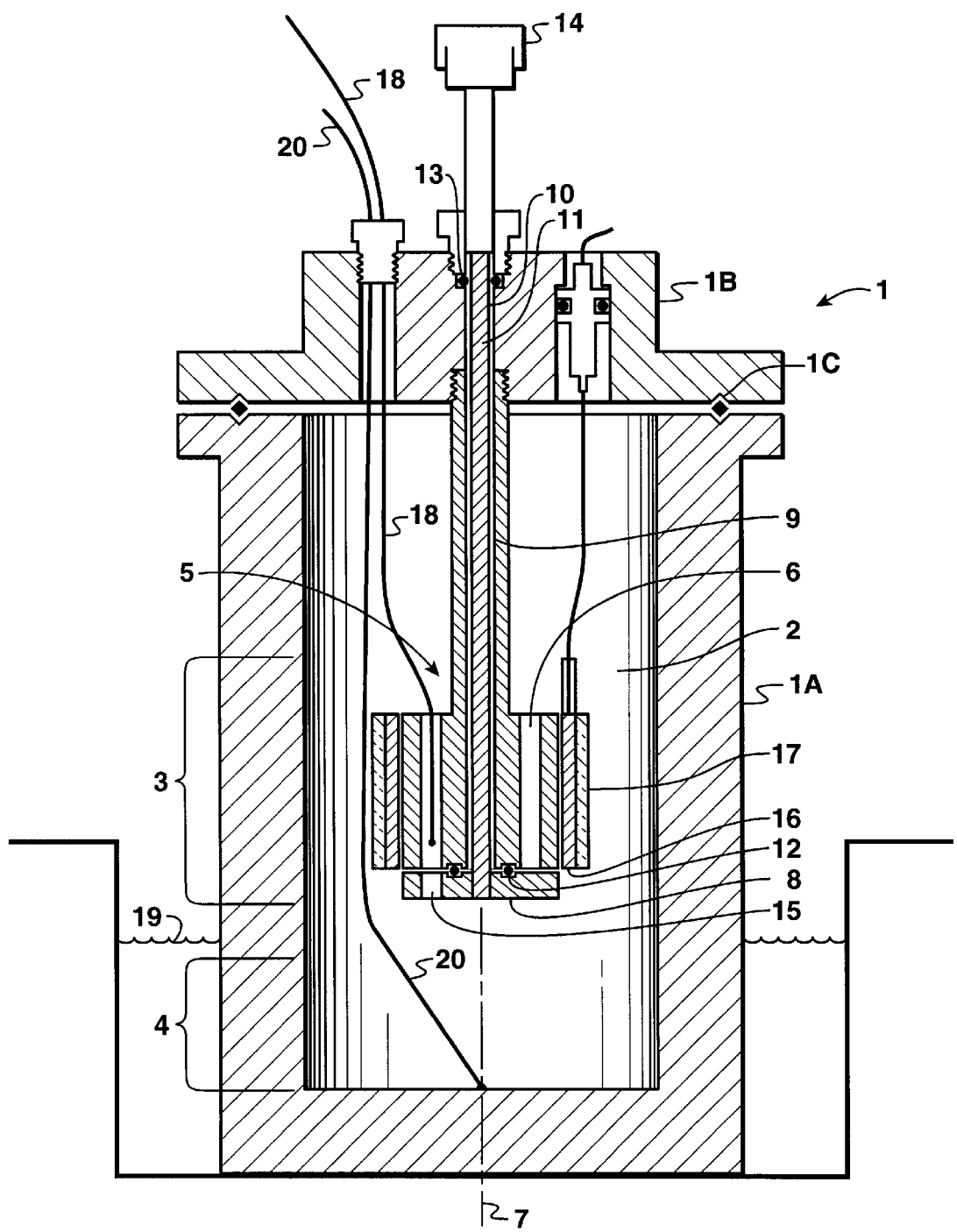
FIG. 1 is a vertical cross-section drawing illustrating an embodiment of the invention in which a pressure vessel is used to control pressure on the sample.

FIG. 1 shows one embodiment of the invention. A pressure vessel 1 defines an interior cavity 2. Closure and the pressure seal of the vessel is provided by well known and conventional means. In the embodiment shown in FIG. 1, the pressure vessel 1 consists of a body 1A and a head 1B. The pressure seal is maintained by placing a gasket 1C between the body 1A and the head 1B and securing the head 1B to the body 1A by conventional means. In this embodiment, all components of the reactor that must pass through the vessel wall are provided with sealed entry holes through the head 1B. More information on the pressure vessel 1 of this embodiment and other similarly suited vessels can be found in *Parr Instrument Company* 1991 *Catalog*, 7th ed. page 105. The vessel 1 shown in FIG. 1 is Parr Instrument Company Model 243HC5 of Hasteiloy™ C-276 construction. However, the vessel 1 may be fabricated from any material capable of withstanding the required design operating temperature and pressure. In additional embodiments of the invention, the head 1B may be at the bottom instead of the top of the vessel 1, or vessel 1 may consist of two substantially similar cup-shaped halves joined together in any suitable manner. Also, some or all of the vessel entry holes can be through the body 1A of the vessel instead of the head 1B. The interior cavity 2 as shown contains two distinct temperature regions, a hot zone 3 and a quench zone 4. In the embodiment shown, the hot zone 3 is located above the quench zone 4.

Pressure is provided and maintained in the pressure vessel by any conventional apparatus for controlling pressure. Such means for producing and maintaining pressure are well known to those skilled in the art and are specified based on their ability to provide the pressures required for a given application. For application requiring higher than atmospheric pressure, a conventional compression system, such as but not limited to, a gas booster compression system such as Model PS-30 as shown in *High Pressure Equipment Company, Catalog* #9000, at page 62. Typically, pressure is transferred from the gas compression system to the vessel through a conventional hose and valve assembly (not shown). In another embodiment, the pressure of the interior cavity 2 is controlled to at or below atmospheric pressure. The vessel 1 can be operated at a vacuum by any conventional device used for maintaining a closed system at or below atmospheric pressure. In the case where operation at atmospheric pressure is desired, the vessel 1 can be sealed at atmospheric pressure without further external means of pressure control, or the vessel 1 can be vented directly to the atmosphere. For applications where operation at atmospheric pressure is desired, the vessel 1 design is unimportant since the function of the vessel 1 in this case is primarily for structural support.

Figure 3B:
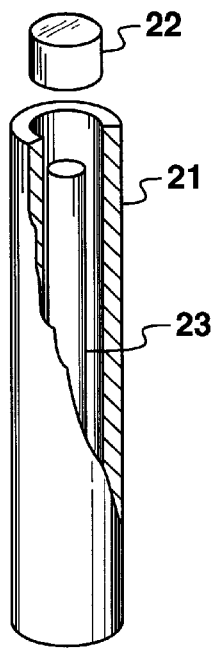
FIG. 3B illustrates a preferred embodiment of a sample enclosure for the embodiments shown in FIGS. 1 and 2.
Figure 3A:
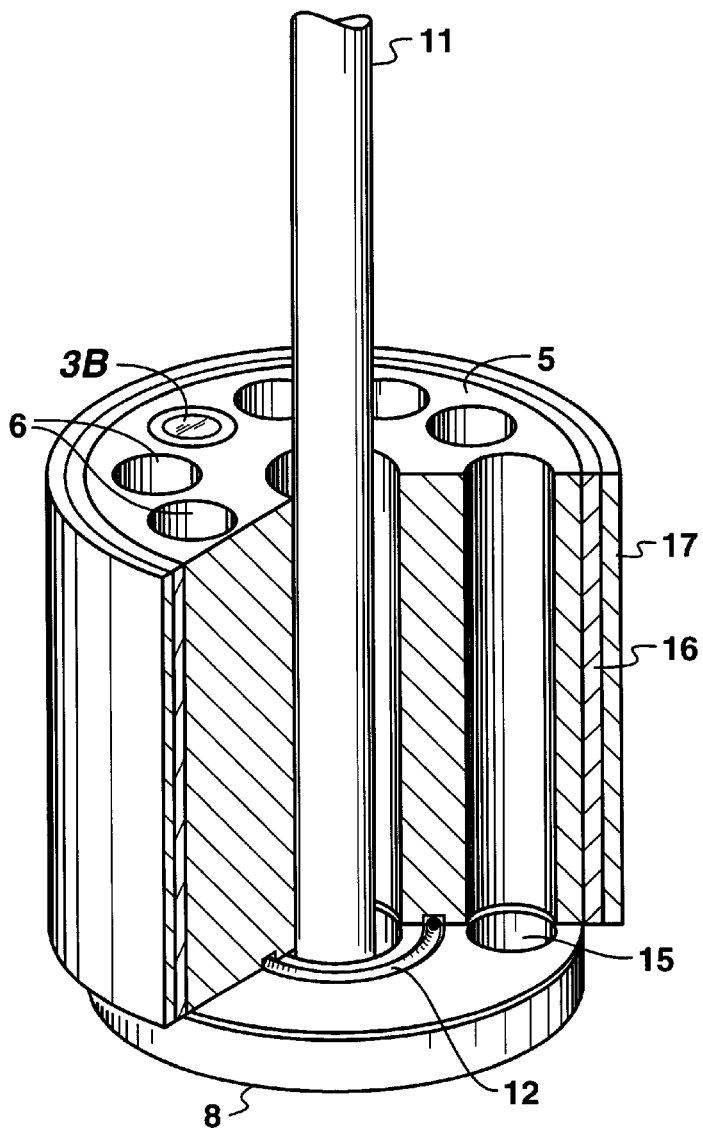
FIG. 3A is a cutaway perspective drawing showing an expanded view of the sample holder and related elements for the embodiments shown in FIGS. 1 and 2.

In the embodiment shown in FIG. 1, a sample holder 5 is mounted in a fixed position within the hot zone 3. The sample holder 5 contains a plurality of sample chambers 6 arranged in a circular pattern about a generally vertical axis of rotation 7. The chambers 6 in the embodiment of the invention shown in FIG. 1 are cylindrical holes having generally vertical longitudinal axes. A sample retaining support 8 is provided to prevent samples from falling from the sample holder 5 into the quench zone 4. In FIG. 1, the support 8 is shown as a flat plate rotatably mounted in close proximity to a flat surface on the underside of the sample holder 5. The sample holder 5 and support 8 as shown in FIGS. 1, and 3A are custom fabricated to the desired dimensions from 316L grade stainless steel bar stock. However, these components may be fabricated from any material capable of withstanding the required design operation temperature of the reactor.

The sample holder 5 in the embodiment shown in FIG. 1 is secured rigidly to the vessel head 1B and has a continuous bore 9 coaxial with the axis of rotation 7 extending from the bottom of the holder 5 to the vessel head 1B. An entry hole 10 in the head 1B of the vessel 1 forms a continuous passageway with bore 9. A control rod 11 passes through this continuous passageway. The lower end of the control rod 11 is rigidly attached to the support 8. The control rod 11 is held in place longitudinally but allowed to rotate about the axis of rotation 7 by a bearing assembly 12 placed between the support 8 and the bottom surface of the holder 5. In the embodiment shown in FIG. 1, placement of the bearing assembly 12 between the lower surface of the holder 5 and the upper surface of the support is particularly preferred in order to provide free rotation of the control rod 11 when the reactor is operated at high pressures. The bearing assembly 12 can be constructed of metal, ceramic, or any material or combination of materials suitable for withstanding the stress and temperature required for maximum operating design conditions for the reactor. In this embodiment, the bearings used are Grade C25 ceramic (alumina) balls, 0.125 inches (3.2 mm) in diameter, available from Hoover Precision Products, Sault Ste. Marie, Mich. A seal 13 is used to prevent loss of pressure between the control rod 11 and the entry hole 10. The upper end of the control rod is attached to a support rotation controller 14. The rotation controller 14 is supported in a fixed position relative to the pressure vessel 1 and can be manually operated or, as in a preferred embodiment, can be driven in an automated fashion by an electric motor driver attached to the upper end of said control rod 11. Ideally, the motor driver is controlled by a timer (not shown) without the need for human intervention during the entire test whereby individual samples are quenched at preselected and different times. As the support plate 8 is rotated by the rotation controller 14, a support plate hole 15 sequentially aligns with each of the holder chambers 6. The support plate hole 15 is sized to allow individual samples placed within the holder chambers 6 to drop into the quench zone 4 when the hole and the relevant chamber are aligned. The control rod 11 as shown in FIGS. 1 and 3A is custom fabricated to the desired specifications from 316L grade stainless steel bar stock. However, the rod 11 may be fabricated from any material capable of withstanding the required design operation temperature of the reactor.

The temperature of samples placed in the chambers 6 in the sample holder 5 is maintained by any known heating device. Preferably, the heating device fits inside the vessel 1 and encases to the greatest extent practical the holder 5. In the embodiment shown in FIG. 1, the heating device is a coiled cable heater 16 wound around the outside surface of the holder 5. Suitable coiled cable heaters include but are not limited to custom fabricated coiled cable heaters, and also band heaters available from Watlow Electric Manufacturing Company, St. Louis, Missouri, and shown in Watlow Electric Manufacturing Company, Catalog COR-HPC-65 (cable heaters on pages 49–56 and band heaters on pages 15–48). In another embodiment, heat may also be supplied to the samples by impedance heating (i.e. using the holder itself as the heat source). Preferably, control of the sample temperature is further improved by encasing to the extent practical the exterior of the combined assembly of the holder 5, support 8, and heater 16 with insulation 17. Sample temperature control can be further improved by installation of sample-monitoring thermocouples 18 within the sample chambers 6 for feedback control of the heating device 16. Suitable thermocouples include but are not limited to sheathed thermocouples, Model KMQSS-040-U-24, available from Omega Engineering Company, Stamford, Conn., and shown in *Omega Engineering Company, Catalog Vol.* 27, page A10 (1989). Any suitable means for installing the sample-monitoring thermocouples 18 through the vessel wall and monitoring the temperatures of the samples from the exterior of the vessel 1 may be used. Such means must be capable of maintaining the pressure integrity of vessel 1.

Additional features or parameters that can be considered and added to the present embodiment, either alone or in any combination, to meet specific testing requirements include, but are not limited to: minimizing the thermal mass of the vessel 1; minimizing the thermal mass of the sample holder 5; and minimizing the clearance or void space between the combined assembly of the holder 5, support 8, heater 16, and insulation 17 and the walls of the vessel 1. Each of these features contributes to the ability of the invention to achieve increased controlled heating rates. Preferably, the invention has the capability of heating samples at rates ranging from less than 1° C. per minute to greater than 50° C. per minute. Although any medium that does not hinder operation of the furnace can be used for pressuring the vessel cavity 2, helium gas is particularly preferred due to its reduced load on the heater 16 as compared to other typical mediums such as argon gas. Gases that reduce the load on the heater are preferred where higher operating temperatures are desired.

Control of the quench zone 4 temperature is maintained by any known cooling system. Suitable cooling systems include, but are not limited to, simple air cooling by displacing the samples a distance from the holder 5 and heater 16 combination, immersion of a portion of the vessel in a cooling medium, or insertion into the vessel cavity 2 at the quench zone 4 of a closed loop heat exchange system. Any of these systems are well known to those skilled in the art and would be specified based on their ability to produce the desired cooling rate. The cooling system provided in the embodiment shown in FIG. 1 includes immersing the lower portion of the vessel 1 in a water bath 19. Preferably, the quench zone 4 temperature is monitored by a quench-zone thermocouple 20, thus allowing feedback for control of the water bath 19 temperature. Suitable thermocouples include but are not limited to sheathed thermocouples identified above. Any suitable means for installing the quench zone thermocouple 20 through the vessel wall and monitoring the quench zone 4 temperature from the exterior of the vessel 1 may be used. For certain applications of the invention, particularly fast cooling of the samples, or quench rates, are preferred. The rate of heat removal from the samples is increased by reducing the temperature of the quench zone 4. Preferably, the quench zone 4 is maintained at or below room temperature, more preferably at or below 15° C.

Figure 2:
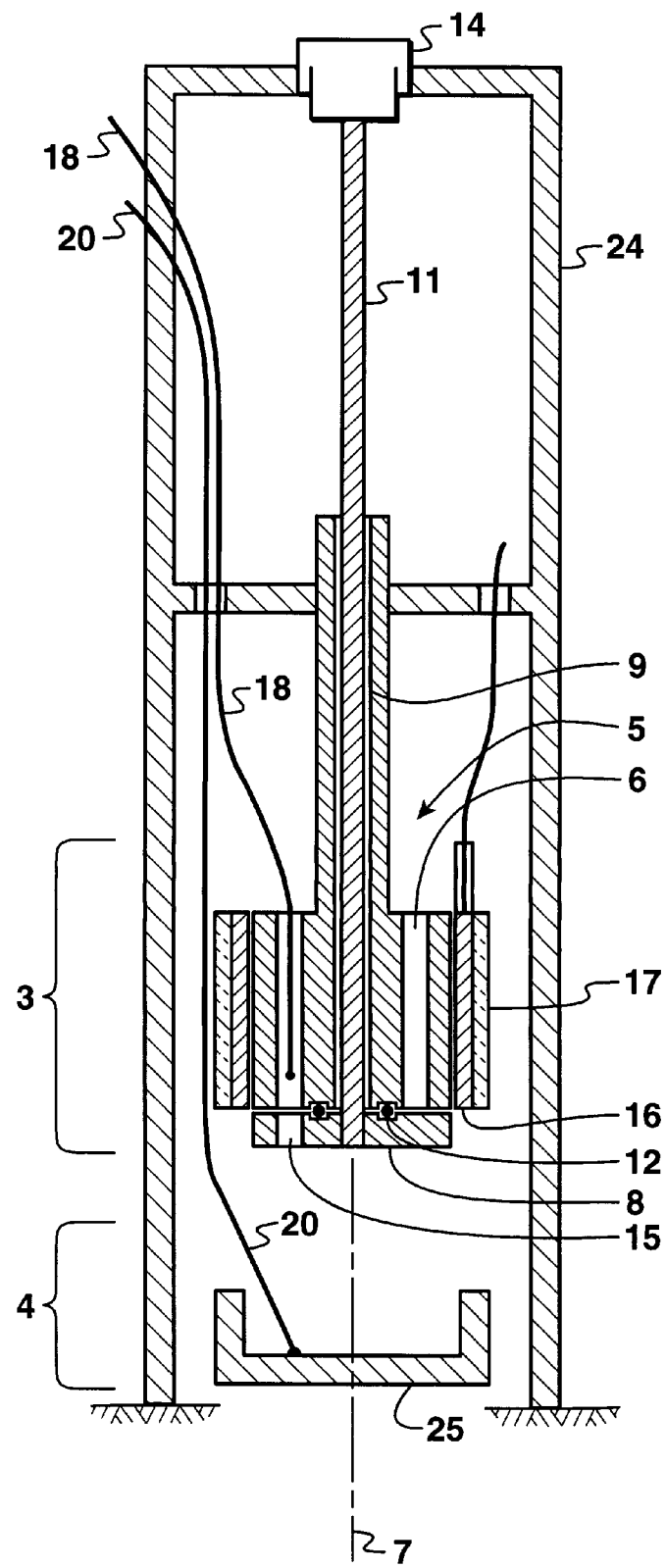
FIG. 2 is a vertical cross-section drawing illustrating another embodiment of the invention in which the sample is exposed to atmospheric pressure.

FIG. 2 shows another embodiment of the invention in which the pressure vessel is omitted and the sample capsules are exposed to ambient pressure conditions. Reference numbers used in FIG. 1 are used to identify the same features in FIG. 2. A support structure 24 directly supports the heating device 16 and the sample holder 5. The support structure 24 may be an open-air structure as shown in FIG. 2 or a full or partial enclosure. The primary function of the support structure 24 is to hold the other parts of the invention in position as described below. Two distinct temperature regions are also present in this embodiment as shown in FIG. 2. The hot zone 3 is again located above the quench zone 4.

In the embodiment shown in FIG. 2, the sample holder 5 is mounted in the support structure 24 at a fixed position within the hot zone 3. The arrangement and function of the sample holder 5, sample chambers 6, bearing assembly 12, the heating device 16, the insulation 17, the control rod 11, the rotation controller 14, the support plate hole 15, and the sample retaining support 8 is substantially identical to the arrangement described above and shown in FIGS. 1 and 3A. The primary difference from the embodiment shown in FIG. 1 is that the sample holder 5 in the embodiment shown in FIG. 2 is secured rigidly to the support structure 24 instead of to a pressure vessel. The rotation controller 14 can be mounted directly to the support structure 24 or otherwise supported in a fixed position relative to the support structure 24. Support for the sample retaining support 8 is provided by connection to the rotation controller 14 through the control rod 11. The bearing assembly 12 does not have to be as durable as the embodiment of FIG. 1 due to the absence of thrust load induced by the difference between internal and external pressures. In other embodiments, the bearing assembly 12 may be omitted entirely. Preferably, a sample-monitoring thermocouple 18 and quench-zone thermocouple 20 are also included as shown.

In this embodiment, the quench zone 4 contains a cooling receptacle 25. The cooling receptacle 25 can be constructed from a metal mesh to maximize the exposure of an ejected sample to ambient air or it may be a solid metal dish, either empty or containing a selected cooling medium. The cooling receptacle 25 can be any distance from the sample holder 5 and further may be movable, either automatically or manually, to permit transport of the ejected sample to a location distant from the support structure 24 and sample holder 5 assembly for further treatment of the sample. Preferably, the quench zone 4 temperature is monitored by a quench-zone thermocouple 20, thus allowing feedback for control of the cooling receptacle 25 temperature. Suitable thermocouples include but are not limited to sheathed thermocouples identified above. For certain applications of the invention, particularly fast cooling of the samples, or quench rates, are preferred. The rate of heat removal from the samples is increased by reducing the temperature of the quench zone 4. Preferably, the quench zone 4 is maintained at or below room temperature, more preferably at or below 15° C.

FIG. 3A is an enlarged perspective view of the combined assembly of the sample holder 5, heater 16, insulation 17, support 8, control rod 11 and bearing assembly 12 as shown in both FIGS. 1 and 2. Minimizing free space between the samples and the sides of the chambers 6 allows the sample to be maintained at a more uniform temperature along its length. In a preferred embodiment, the homogeneity of the sample temperature is maximized by enclosing the sample capsule 23 in a brass enclosure 21 and capping the enclosure 21 with a glass insulating plug 22, as illustrated in FIG. 3B. The sample capsule 23 can be fabricated from any material suitable to withstand the conditions of the experiment, without contaminating the enclosed sample. Noble metals are chemically inert and deformable, transmitting pressure to the contents of the capsule 23. Experiments conducted at atmospheric pressure can utilize fused silica tubes as sample capsules in addition to the use of noble metal capsules.

For embodiments of the invention either with or without a pressure vessel, one skilled in the art would recognize that other holder and support arrangements could be devised to selectively drop individual samples into the quench zone 4. For example, in another embodiment the sample holder rotates about a horizontal axis. The sample chambers are open slots on the outer cylindrical surface of the holder. The sample retaining support is a curved plate mounted in a fixed position and shaped to fit closely to the outer diameter of the sample holder. The support in this embodiment has a slotted hole which sequentially aligns with the slots in the holder as the holder is rotated about its horizontal axis of rotation, thus allowing individual samples to drop into the quench zone.

Various component designs and spatial orientations will provide a sample release mechanism for selectively and independently moving individual reactant samples from said holder to said quench zone. The sample holder will have at least two chambers suitable for holding samples, preferably more, arranged in a pattern such that movement of the sample retaining support relative to the sample holder will allow an opening in the holder to align with each of the chambers at some point in the path of the relative motion of the holder and the support. Preferably, the pattern will be circular, and the relative motion will be rotation of the two components with respect to each other about a common axis of rotation. When the opening is not aligned with an individual chamber, the support will prevent a sample contained in that chamber from dropping into the quench zone. The opening in the support is suitably any shape (e.g. slot, circular hole, notch, among others) provided that the relative motion of the holder and the support causes the opening to align with each of the chambers at some point in the movement and that alignment of the opening with the chamber will allow the sample in that chamber to drop to the quench zone.

The above embodiments are directed to reactors where samples of the same material are subjected to the same temperature and pressure conditions, and individual samples may be quenched at different times. These times may represent points along a heating profile with samples being quenched sequentially at higher temperatures. In another embodiment of the invention, samples of different materials are subjected to the same temperature and pressure conditions, but all the samples are quenched at the same time. The invention also includes variations of the above embodiments wherein more than one, but less than all samples, are quenched simultaneously. In all embodiments, the pressure and temperature conditions can be constant, have preselected rates of change, or a combination of both.

As described above, the present invention satisfies the need for equipment capable of simultaneously performing experiments upon multiple samples while varying conditions of pressure, temperature, and time. It should be understood that the invention is not to be unduly limited to the foregoing which has been set forth for illustrative purposes. Various modifications and alterations of the invention will be apparent to those skilled in the art without departing from the true scope of the invention as defined in the following claims. For example, a reactor could be designed in which the hot zone is located beside the quench zone rather than above it. In such a reactor, some means other than gravity would be needed to selectively and individually move the samples from the hot zone to the quench zone.

What is claimed is:

1. A reactor for simultaneously subjecting a plurality of reactant samples to controlled temperature conditions, said reactor comprising:

a) a support structure surrounding a region comprising a hot zone located above a quench zone;

b) a heating device for said hot zone;

c) a cooling system for said quench zone;

d) a sample holder mounted within said hot zone and comprising a plurality of chambers arranged in a circular pattern and adapted to hold a plurality of reactant samples; and e) a sample release mechanism which can be rotated with respect to said sample holder about a common axis which passes through the center of said circular pattern and is capable of selectively and independently moving individual reactant samples from said holder to said quench zone.

2. The reactor of claim 1 wherein said sample release mechanism comprises a support having an opening, said sample holder and said support mounted in relation to one another such that:

a) said support is capable of retaining samples placed within said chambers; and b) rotation of said holder and said sample release mechanism with respect to one another causes sequential positioning of said opening with respect to each of said chambers such that samples retained in said chambers would move from said holder to said quench zone.

3. The reactor of claim 2 wherein:

a) said holder is substantially cylindrical;

b) said axis is substantially vertical;

c) said chambers are cylindrical holes parallel to said axis; and d) said support is a plate and said opening is a hole at least as large as said cylindrical holes.

4. The reactor of claim 3 wherein said heating device is a coiled cable heater wound around said holder.

5. The reactor of claim 2 wherein said sample release mechanism further comprises a control rod rotatably mounted coaxially with said axis, and attached at one end to said support and at the other end to an electric motor driver controlled by a timer.

6. The reactor of claim 1 wherein said support structure is a vessel defining a cavity and surrounding said hot zone and said quench zone, said reactor further comprising a pressure control apparatus suitable for controlling the pressure in said cavity.

7. The reactor of claim 6 wherein said pressure control apparatus is a gas compression system.

8. The reactor of claim 6 wherein said cooling system comprises substantially immersing the quench zone portion of the reactor in a water bath.

9. A reactor for simultaneously subjecting a plurality of reactant samples to controlled pressure and temperature conditions, said reactor comprising:
   a) a pressure vessel, defining a cavity comprising a hot zone and a quench zone, said hot zone located substantially above said quench zone;
   b) a gas compression system connected by hose to said vessel;
   c) a substantially cylindrical sample holder, mounted within said hot zone and comprising a plurality of cylindrical holes substantially parallel to said axis and arranged in a circular pattern, each hole adapted to hold individual samples;
   d) a sample retaining support comprising a plate having a hole at least as large as said cylindrical holes in said holder, said plate mounted in relation to said holder such that
      i) said plate can be rotated with respect to the holder about a substantially vertical common axis which passes through the center of said circular pattern,
      ii) said plate is capable of retaining samples placed within said chambers, and
      iii) rotation of said plate causes sequential positioning of said plate hole with respect to each of the chambers such that samples retained in said chambers would drop from said holder to said quench zone;
   e) a coiled cable heater wound around said holder to provide heat to said sample chambers; and
   f) a water bath for cooling said quench zone by substantially immersing the quench zone portion of the reactor in said water bath.

10. The reactor of claim 9 further comprising a electric motor driver controlled by a timer to automatically move samples from said hot zone to said quench zone at preselected times.

11. A reactor for simultaneously subjecting a plurality of reactant samples to controlled temperature conditions at atmospheric pressure, said reactor comprising:
   a) a sample holder mounted on a support structure and comprising a plurality of chambers arranged in a circular pattern and adapted to hold a plurality of reactant samples;
   b) a heating device for said sample holder and any reactant samples held within said sample holder;
   c) a sample release mechanism which can be rotated with respect to said sample holder about a common axis which passes through the center of said circular pattern and is used for selectively and independently moving individual reactant samples from said sample holder; and
   d) a cooling system located below said sample holder and used for said reactant samples after removal from said sample holder.

12. The reactor of claim 11 wherein said sample release mechanism comprises a support having an opening, said sample holder and said support mounted in relation to one another such that:
   a) the support is capable of retaining samples placed within said chambers; and
   b) rotation of the holder and the sample release mechanism with respect to one another causes sequential positioning of the opening with respect to each of the chambers such that samples retained in said chambers would drop from the holder to the quench zone.

13. The reactor of claim 12 wherein:
   a) said holder is substantially cylindrical;
   b) said axis is substantially vertical;
   c) said chambers are cylindrical holes parallel to said axis; and
   d) said support is a plate and said opening is a hole at least as large as said cylindrical holes.

14. The reactor of claim 13 wherein said heating device is a coiled cable heater wound around said holder.

15. The reactor of claim 12 wherein said sample release mechanism further comprises a control rod rotatably mounted coaxially with said axis, and attached at one end to said support and at the other end to an electric motor driver controlled by a timer.

* * * * *